United States Patent
Goldring et al.

(10) Patent No.: US 9,291,504 B2
(45) Date of Patent: Mar. 22, 2016

(54) SPECTROMETRY SYSTEM WITH DECREASED LIGHT PATH

(71) Applicant: VERIFOOD, LTD., Herzliya (IL)

(72) Inventors: Damian Goldring, Tel-Aviv (IL); Dror Sharon, Benei Atarot (IL); Guy Brodetzki, Rehovot (IL); Amit Ruf, Hod HaSharon (IL); Menahem Kaplan, Tel-Aviv (IL); Sagee Rosen, Netzer Sireni (IL); Omer Keilaf, Kfar Saba (IL); Uri Kinrot, Hod HaSharon (IL); Kai Engelhardt, Buckenhof (DE); Ittai Nir, Tel-Aviv (IL)

(73) Assignee: VERIFOOD, LTD., Herzlita (IL)

(*) Notice: Subject to any disclaimer, the term of this patent is extended or adjusted under 35 U.S.C. 154(b) by 0 days.

(21) Appl. No.: 14/702,342

(22) Filed: May 1, 2015

(65) Prior Publication Data
US 2015/0355024 A1 Dec. 10, 2015

Related U.S. Application Data

(63) Continuation of application No. PCT/IL2014/050688, filed on Jul. 30, 2014.

(60) Provisional application No. 61/861,893, filed on Aug. 2, 2013, provisional application No. 61/923,422, filed on Jan. 3, 2014, provisional application No. 61/985,447, filed on Apr. 28, 2014.

(51) Int. Cl.
*G01J 3/28* (2006.01)
*G01J 3/45* (2006.01)
(Continued)

(52) U.S. Cl.
CPC ............. *G01J 3/45* (2013.01); *G01J 3/0205* (2013.01); *G01J 3/0208* (2013.01); *G01J 3/0256* (2013.01);
(Continued)

(58) Field of Classification Search
CPC .............. G01J 3/02; G01J 3/28; G01J 3/18; G01J 3/10; G01J 3/2803; G01J 3/2823
USPC .................................................. 356/300–445
See application file for complete search history.

(56) References Cited

U.S. PATENT DOCUMENTS

| 679,577 A | 7/1901 | Henry |
|---|---|---|
| 5,469,252 A | 11/1995 | Doles et al. |

(Continued)

FOREIGN PATENT DOCUMENTS

| WO | WO 99/53350 A1 | 10/1999 |
|---|---|---|
| WO | WO-2010027982 A2 | 3/2010 |

(Continued)

OTHER PUBLICATIONS

U.S. Appl. No. 14/702,422, filed May 1, 2015, Goldring et al.

(Continued)

*Primary Examiner* — Abdullahi Nur
(74) *Attorney, Agent, or Firm* — Wilson, Sonsini, Goodrich & Rosati

(57) ABSTRACT

A spectrometer comprises a plurality of isolated optical channels comprising a plurality of isolated optical paths. The isolated optical paths decrease cross-talk among the optical paths and allow the spectrometer to have a decreased length with increased resolution. In many embodiments, the isolated optical paths comprise isolated parallel optical paths that allow the length of the device to be decreased substantially. In many embodiments, each isolated optical path extends from a filter of a filter array, through a lens of a lens array, through a channel of a support array, to a region of a sensor array. Each region of the sensor array comprises a plurality of sensor elements in which a location of the sensor element corresponds to the wavelength of light received based on an angle of light received at the location, the focal length of the lens and the central wavelength of the filter.

21 Claims, 8 Drawing Sheets

(51) Int. Cl.
*G01J 3/10* (2006.01)
*G01J 3/02* (2006.01)
*G01J 3/12* (2006.01)
*G01J 3/26* (2006.01)
*G01N 21/25* (2006.01)

(52) U.S. Cl.
CPC ............ *G01J 3/0262* (2013.01); *G01J 3/0264* (2013.01); *G01J 3/0272* (2013.01); *G01J 3/10* (2013.01); *G01J 3/12* (2013.01); *G01J 3/26* (2013.01); *G01J 3/2803* (2013.01); *G01J 2003/1226* (2013.01); *G01N 21/255* (2013.01)

(56) References Cited

U.S. PATENT DOCUMENTS

| | | | |
|---|---|---|---|
| 6,031,233 A | 2/2000 | Levin et al. | |
| 6,031,619 A | 2/2000 | Wilkens et al. | |
| 6,212,312 B1 | 4/2001 | Grann et al. | |
| 6,483,583 B1 | 11/2002 | Wright et al. | |
| 7,236,243 B2 | 6/2007 | Beecroft et al. | |
| 7,262,839 B2 | 8/2007 | Treado et al. | |
| 7,286,233 B2 | 10/2007 | Pizzi | |
| 7,414,724 B2 | 8/2008 | Eckert et al. | |
| 7,420,663 B2 | 9/2008 | Wang et al. | |
| 7,433,042 B1* | 10/2008 | Cavanaugh | G01J 3/02 356/419 |
| 7,528,957 B2 | 5/2009 | Lewis et al. | |
| 7,535,617 B2 | 5/2009 | Gupta et al. | |
| 7,667,740 B2 | 2/2010 | Hofer | |
| 7,805,319 B2 | 9/2010 | Badinelli | |
| 7,897,923 B2 | 3/2011 | Shelley et al. | |
| 7,986,193 B2 | 7/2011 | Krah | |
| 8,060,383 B2 | 11/2011 | Badinelli | |
| 8,149,415 B2 | 4/2012 | Sanders et al. | |
| 8,269,174 B2 | 9/2012 | Gardner, Jr. et al. | |
| 8,274,739 B2 | 9/2012 | Lee et al. | |
| 8,284,401 B2 | 10/2012 | Choi et al. | |
| 8,330,945 B2 | 12/2012 | Choi et al. | |
| 8,462,420 B2 | 6/2013 | Lee et al. | |
| 8,542,359 B2 | 9/2013 | Choi et al. | |
| 8,665,440 B1 | 3/2014 | Kompaniets et al. | |
| 9,060,113 B2 | 6/2015 | Rhoads et al. | |
| 2002/0039186 A1 | 4/2002 | Rosenberg | |
| 2002/0131047 A1 | 9/2002 | Zarrabian et al. | |
| 2002/0163641 A1 | 11/2002 | Shroder | |
| 2002/0191127 A1 | 12/2002 | Roberts et al. | |
| 2004/0136577 A1 | 7/2004 | Rao et al. | |
| 2005/0151975 A1* | 7/2005 | Melnyk | G01B 11/18 356/480 |
| 2005/0196046 A1 | 9/2005 | Hudnut et al. | |
| 2006/0086901 A1 | 4/2006 | Price et al. | |
| 2006/0124656 A1 | 6/2006 | Popovich | |
| 2006/0146315 A1 | 7/2006 | Treado | |
| 2007/0230932 A1 | 10/2007 | Tanaka et al. | |
| 2008/0061236 A1 | 3/2008 | Meredith et al. | |
| 2008/0073510 A1 | 3/2008 | Finlay | |
| 2008/0137328 A1* | 6/2008 | Lee | G02B 6/0078 362/224 |
| 2008/0204578 A1 | 8/2008 | Scheuch et al. | |
| 2008/0277625 A1 | 11/2008 | Nakamura et al. | |
| 2009/0201577 A1 | 8/2009 | Laplante et al. | |
| 2010/0110442 A1 | 5/2010 | Adibi et al. | |
| 2010/0128370 A1 | 5/2010 | Chen et al. | |
| 2010/0134794 A1 | 6/2010 | Odegard et al. | |
| 2010/0191493 A1 | 7/2010 | Brown et al. | |
| 2010/0201979 A1 | 8/2010 | Momtahan et al. | |
| 2010/0271352 A1 | 10/2010 | Nakano et al. | |
| 2010/0284005 A1 | 11/2010 | Malinen et al. | |
| 2010/0309454 A1 | 12/2010 | Zhang | |
| 2011/0255745 A1 | 10/2011 | Hodder et al. | |
| 2011/0261252 A1 | 10/2011 | Chen | |
| 2011/0318717 A1 | 12/2011 | Adamowicz | |
| 2012/0018829 A1 | 1/2012 | Beck et al. | |
| 2012/0019819 A1 | 1/2012 | Messerchmidt | |
| 2012/0053426 A1 | 3/2012 | Webster et al. | |
| 2012/0088486 A1 | 4/2012 | Messerchmidt | |
| 2013/0021611 A1 | 1/2013 | Tsurutani | |
| 2013/0155402 A1 | 6/2013 | Walton et al. | |
| 2014/0052555 A1 | 2/2014 | Macintosh | |
| 2014/0293091 A1 | 10/2014 | Rhoads et al. | |
| 2014/0320858 A1 | 10/2014 | Goldring et al. | |
| 2015/0036138 A1 | 2/2015 | Watson et al. | |
| 2015/0055132 A1 | 2/2015 | Ricketts et al. | |
| 2015/0204833 A1 | 7/2015 | O'Brien et al. | |
| 2015/0233762 A1 | 8/2015 | Goldring et al. | |
| 2015/0292948 A1 | 10/2015 | Goldring et al. | |
| 2015/0300879 A1 | 10/2015 | Goldring et al. | |

FOREIGN PATENT DOCUMENTS

| | | |
|---|---|---|
| WO | WO-2013065035 A1 | 5/2013 |
| WO | WO 2015/015493 A2 | 2/2015 |
| WO | WO-2015101992 A2 | 7/2015 |

OTHER PUBLICATIONS

U.S. Appl. No. 14/702,461, filed May 1, 2015, Goldring et al.
U.S. Appl. No. 14/702,470, filed May 1, 2015, Goldring et al.
Acktar Advanced Coatings Website. Accessed Jun. 3, 2015. http://www.acktar.com/.
Anoplate Website. Accessed Jun. 3, 2015. http://www.anoplate.com/capabilities/anoblack_ni.html.
Avian Technologies Website. Accessed Jun. 3, 2015. http://www.aviantechnologies.com/products/coatings/diffuse_black.php.
International search report and written opinion dated Jan. 26, 2015 for PCT Application No. IL2014/050688.
International search report and written opinion dated Mar. 22, 2013 for PCT Application No. IL2012/000367.
"Interference Filter Handbook," published by JDS Uniphase (Second Edition), Sep. 2006, p. 195-202 and 213-214.
International search report and written opinion dated Jul. 14, 2015 for PCT Application No. PCT/IL2015/050002.
Office action dated Oct. 21, 2015 for U.S. Appl. No. 14/702,422.
Office action dated Oct. 21, 2015 for U.S. Appl. No. 14/702,461.
Office action dated Oct. 30, 2015 for U.S. Appl. No. 14/702,470.

* cited by examiner

SPECTROMETRY SYSTEM WITH DECREASED LIGHT PATH

CROSS-REFERENCE

The present application is a continuation of PCT Application PCT/IL2014/050688, filed on Jul. 30, 2014, entitled "Spectrometry System and Method, Spectroscopic Devices and Systems", which claims priority to U.S. Provisional Application Ser. No. 61/861,893, filed on Aug. 2, 2013, entitled "Spectrometer System", U.S. Provisional Application Ser. No. 61/923,422, filed on Jan. 3, 2014, entitled "Spectroscopic Devices and Systems", and U.S. Provisional Application Ser. No. 61/985,447 filed on Apr. 28, 2014, entitled "Spectroscopic Devices and Systems", each of which is incorporated herein by reference in its entirety.

INCORPORATION BY REFERENCE

All publications, patents, and patent applications mentioned in this specification are herein incorporated by reference to the same extent as if each individual publication, patent, or patent application was specifically and individually indicated to be incorporated by reference.

FIELD OF THE INVENTION

This invention relates to small, low-cost spectrometry systems. For example, it relates to hand-held systems that have sufficient sensitivity and resolution to perform spectroscopic analysis of substances (including complex mixtures, e.g. foodstuffs).

BACKGROUND OF THE INVENTION

Spectrometers are used for many purposes. For example spectrometers are used in the detection of defects in industrial processes, satellite imaging, and laboratory research. However these instruments have typically been too large and too costly for the consumer market.

Spectrometers detect radiation from a sample and process the resulting signal to obtain and present information about the sample that includes spectral, physical and chemical information about the sample. These instruments generally include some type of spectrally selective element to separate wavelengths of radiation received from the sample, and a first-stage optic, such as a lens, to focus or concentrate the radiation onto an imaging array.

The prior spectrometers can be less than ideal in at least some respects. Prior spectrometers having high resolution can be larger than ideal for use in many portable applications. Also, the cost of prior spectrometers can be greater than would be ideal. The prior spectrometers can be somewhat bulky, difficult to transport and the optics can require more alignment than would be ideal in at least some instances.

Although prior spectrometers with decreased size have been proposed. The prior spectrometers having decreased size and optical path length can have less than ideal resolution, sensitivity and less accuracy than would be ideal.

In light of the above, it an improved spectrometer that overcomes at least some of the above mentioned deficiencies of the prior spectrometers would be beneficial. Ideally such a spectrometer would be a compact, integrated with a consumer device such as a cellular telephone, sufficiently rugged and low in cost to be practical for end-user spectroscopic measurements of items, convenient and convenient to use.

SUMMARY OF THE INVENTION

Embodiments of the present disclosure provide an improved spectrometer, such as a low-cost, rugged spectrometer suitable for combination with consumer devices and cloud computing. In many embodiments, the spectrometer comprises a plurality of isolated optical channels comprising a plurality of isolated optical paths. The isolated optical paths have the advantage of decreasing cross-talk among the optical paths and allowing the spectrometer to have a decreased length with increased resolution. In many embodiments, the isolated optical paths comprise isolated parallel optical paths that allow the length of the device to be decreased substantially. In many embodiments, each isolated optical path extends from a filter of a filter array, through a lens of a lens array, through a channel of a support array, to a region of a sensor array. Each region of the sensor array comprises a plurality of sensor elements in which a location of the sensor element corresponds to the wavelength of light received based on an angle of light received at the location, the focal length of the lens and the central wavelength of the filter. In many embodiments, a diffuser is located along the optical path prior to the filter array in order to provide at least constant angular distribution of light energy among the filters of the array. In many embodiments, a second diffuser is located along the optical path between the diffuser and the filter at a sufficient distance from the diffuser in order to receive a substantially uniform distribution of light energy across the second diffuser in order to further homogenize the light and provide a constant angular distribution of the light energy transmitted to the filter array.

In many embodiments, the spectrometer system provides a substantially straight optical axis and a short light path. The straight optical axis and short light path enable production of spectrometers that are small enough and economical enough to fit in devices such as cellular phones, and yet have sufficient sensitivity and resolution (e.g. <10 nm) to obtain useful spectra of complex mixtures.

In many embodiments a compact spectrometer system for obtaining the spectrum of a sample comprises (a) an optical detector for detecting light emanating from said sample; (b) an optical filter located between said sample and said detector; and (c) a first Fourier transform focusing element, wherein said compact spectrometer system does not contain any dispersive optical elements.

In one aspect, provided herein is a spectrometer, the spectrometer comprising: a plurality of isolated optical paths extending from a filter array to a sensor array. In many embodiments, the spectrometer further comprises: a plurality of regions of the sensor array; a plurality of filters of the filter array; a plurality of lenses of a lens array; and a support array extending between the plurality of regions of the sensor array and the plurality of lenses of the lens array, the support array comprising a plurality of light transmitting channels defined with a non-optically transmissive material, wherein the plurality of isolated optical paths extends from the plurality of lenses through the plurality of channels to the plurality of regions in order to isolate the plurality of channels.

In another aspect, provided herein is a spectrometer comprising: a diffuser; a detector comprising a plurality of regions, each region of said plurality of regions comprising multiple sensors; a lens array comprising a plurality of lenses, each lens of the lens array corresponding to a region of said plurality of regions; and a filter array corresponding to the lens array, the filter array comprising a plurality of filters, wherein each filter of the plurality of filters is configured to transmit a range of wavelengths different from other filters of the plurality.

In many embodiments, the range of wavelengths overlaps with ranges of said other filters of the plurality and wherein said each filter comprises a central wavelength different from said other filters of the plurality.

In many embodiments, the plurality of filters comprises a plurality of interference filters, the plurality of interference filters arranged with the plurality of lenses to vary an optical path length through each of the interference filters in order to determine spectra of each of the plurality of regions.

The filter array can comprise a substrate having a thickness and a first side and a second side, the first side oriented toward the diffuser, the second side oriented toward the lens array and detector, wherein the filter array comprises a plurality of coatings on the second side oriented toward the lens array to inhibit cross-talk among lenses of the array.

In many embodiments, the plurality of coatings on the second side comprises a plurality of interference filters, said each of the plurality of interference filters on the second side configured to transmit a central wavelength of light to one lens of the plurality of lenses.

The filter array can comprise one or more coatings on the first side of the filter array, for example, the first side of the array comprises a coating to balance mechanical stress. Alternatively or in combination, the one or more coatings on the first side of the filter array comprises an optical filter. For example, the optical filter on the first side of the filter array comprises an IR pass filter to selectively pass infrared light.

In many embodiments, the first side of the substrate does not comprise a coating.

The spectrometer can further comprise a support extending between the detector and the lens array, the support shaped and sized in order to support the lens array and position the lens array at a focal length from the detector, the support comprising a plurality of channels to pass light from the plurality of lenses of the array to the plurality of regions of the detector.

In many embodiments, the support comprises a light absorbing material located on a wall of said each of the plurality of channels in order to inhibit cross-talk among the plurality of channels.

The support can comprise an axis extending a distance from an upper surface of the detector to a lower surface of the lens array and wherein the support comprises stiffness in order to fix the distance from the upper surface to the lower surface at the focal length.

The image sensor can comprise a bare die surface in contact with the support to position each of the plurality of lenses at the focal length from the bare die surface.

The plurality of regions can comprise a plurality of active regions and wherein the plurality of channels corresponds to the plurality of active regions and wherein the support comprises end structures sized and shaped to contact the bare die surface at a plurality of contact locations away from the plurality of active regions.

The spectrometer described herein can comprise an aperture array comprising a plurality of apertures formed in a non-optically transmissive material, the plurality of apertures dimensioned to define a clear lens aperture of each lens of the array, wherein the clear lens aperture of each lens is limited to one filter of the array.

For example, the clear lens aperture of each lens can be limited to one filter of the array.

In many embodiments, the spectrometer further comprises a filter support to hold the filters plurality of filters in place between the diffuser and the plurality of lenses.

The spectrometer described herein can comprise an optically transmissive plate placed over the plurality of filters to seal the plurality of filters.

In many embodiments, the diffuser is configured to receive incident light from a material of a sample to be analyzed and transmit diffuse light and wherein an angular profile of the transmitted diffuse light is substantially fixed and substantially independent of an angle of incidence of the light from the sample. The diffuser can comprise a cosine diffuser to generate a Lambertian light distribution.

The spectrometer can comprise an IR pass filter composed of an IR transmissive material, wherein the diffuser is formed in a surface of the IR transmissive material.

In many embodiments, the spectrometer further comprises a second diffuser formed in a second surface of the IR transmissive material opposite the surface, wherein the second diffuser distributes incoming light across the diffuser.

The spectrometer can comprise a second IR pass filter and a housing, the housing covering the diffuser, the filter array, and the lens array, wherein the housing is coupled to the second IR pass filter and a support comprising a plurality of apertures and wherein the diffuser, the filter array, and the lens array are arranged sequentially between the second IR pass filter and the support comprising the plurality of apertures in order to couple the support, the filter array and the lens array to a bare surface of the detector.

In many embodiments of the spectrometer described herein, the spectrometer further comprises a processor comprising a tangible medium embodying instructions to determine spectra in response to signals from the detector.

The processor can comprise instructions to stitch together spectra from each of the regions in order to determine a spectrum of a target site of a material.

The spectrometer can further comprise: an illuminator, the illuminator comprising, a) a primary radiation emitter to emit primary radiation within a first wavelength range and, b) a secondary radiation emitter to emit secondary radiation within a second wavelength range different from the first wavelength range.

The primary radiation emitter can comprise one or more of a light emitting diode or a laser diode and wherein the secondary emitter comprises on or more of a phosphorescent plate, a phosphor plate, phosphor powder, nanocrystals, or nano-crystal powder.

The secondary radiation emitter can contact packaging of the primary radiation emitter to inhibit heating of the secondary emitter and wherein the packaging comprises a heat sink to conduct heat away from the secondary radiation emitter.

In many embodiments, a gap extends between the secondary radiation emitter and packaging of the primary radiation emitter to inhibit heating of the secondary emitter.

The spectrometer can comprise a temperature sensor having a field of view oriented to overlap with a field of view of the detector and a field of view of an illuminator.

The illuminator can comprise optics arranged to direct light from the secondary radiation emitter toward a field of view of the detector.

In another aspect, provided herein is a spectrometer assembly comprising: a housing; an optically transmissive cover plate; a diffuser; a filter array comprising a plurality of filters; a lens array comprising plurality of lenses; and a support comprising a plurality of channels; wherein the housing covers the diffuser, the filter array and the lens array with the transmissive cover plate on a first end of the assembly and the support on a second end of the assembly in order to place the support on a detector to measure spectra.

In yet another aspect, provided herein is a spectrometer comprising a light path, the light path passing sequentially through a diffuser, a filter matrix, and a lens array; wherein the light path ends at a detector; wherein the detector comprises multiple sensors; wherein the light path from the diffuser to the detector is less than 9 mm; and wherein the resolution of the spectrometer is less than 20 nm.

A spectrometer comprising a light path, the light path passing sequentially through a diffuser, a filter matrix, and a lens array; wherein the light path ends at a detector; wherein the detector comprises multiple sensors; wherein the light path from the diffuser to the detector is less than 9 mm; and wherein the resolution of the spectrometer is less than 10 nm. The resolution can be less than 25, 24, 23, 22, 21, 20, 19, 18, 17, 16, 15, 14, 13, 12, 10, 9 or 8 nm.

The light path beginning at the diffuser and ending at the detector can be less than 6 mm or less than 4.5 mm.

The resolution of the spectrometer can be less than 8 nm. The resolution of the spectrometer can be less than 5 nm.

The detectable wavelength range can be larger than 100 nm. The detectable wavelength range can be larger than 200 nm. The detectable wavelength range can be larger than 300 nm.

In many embodiments, the spectrometer does not comprise a dispersive optical element.

Also provided herein, is a spectrometer comprising a detector for receiving light wherein the light received by the detector is a noncontiguous spectrum.

The spectrometer can comprise a filter matrix, the filter matrix comprising multiple sub-filters.

In many embodiments, one point on the detector receives light from multiple sub-filters.

The spectrometer provided herein can further comprise a pre-filter before the filter matrix in the light path.

The pre-filter can be chosen from a group consisting of: (a) absorbing glass and (b) interference filter.

In many embodiments, the diffuser can be a cosine diffuser.

A secondary diffuser can be added between the diffuser and the filter matrix.

The distance between the diffuser and the secondary diffuser can be at least 0.5 mm.

In many embodiments, the transmission spectra of the filters in the filter matrix vary with angle of incidence.

The filter matrix can be composed of interference filters.

The interference filters can be deposited on a substrate thinner than 2 mm.

In many embodiments, the interference filters are deposited only on a single side of a substrate.

The deposited side of the interference filters can be facing towards the lens array.

The filters in the filter matrix can be arranged in a specific order to minimize cross talk on the detector of light emerging from different filters.

In many embodiments, the spectrometer can comprise at least one opaque aperture array between the filter matrix and the lens array.

The spectrometer can comprise an opaque absorbing aperture array between the filter matrix and the detector.

The optical surfaces of the lenses in the lens array can be a-spherical.

Individual lens of the lens array can have two optical surfaces where both optical surfaces can be substantially convex.

The spectra of each filter in the matrix can overlap another filter in the matrix.

In many embodiments of the matrix, the overlap can allow stitching of spectra generated by two different filters.

The spectrometer can further comprise an illumination system.

The illumination system can comprise LEDs.

The LEDs can be divided into at least two groups, each operated at different times.

The spectrometer can comprise at least one power resistor for thermal control.

The spectrometer can further comprise a phosphor plate in front of the LEDs.

The phosphor can be near infra-red phosphor.

The spectrometer can comprise a thermal sensor capable of measuring a sampled material's temperature.

In many embodiments, the spectrometer further comprises a reference element in front of the spectrometer.

The reference element can be removable.

The reference element can be movable.

The detector can be a 2D CMOS sensor.

The multiple sensors can be pixels on a CCD.

The multiple sensors can each receive light from more than one narrow wavelength band.

In many embodiments of the spectrometer, the multiple sensors each receive light from more than one filter of the filter matrix.

In another aspect, further provided herein is a method of measuring spectrum, the method comprising: transmitting light along a plurality of isolated optical paths extending from a filter array to a sensor array in order to measure the spectrum.

In many embodiments of the method, the spectrum comprises a plurality of spectra.

Further provided herein is a method, the method comprising providing a spectrometer as described herein.

DETAILED DESCRIPTION OF THE INVENTION

In the following description, various aspects of the invention will be described. For the purposes of explanation, specific details are set forth in order to provide a thorough understanding of the invention. It will be apparent to one skilled in the art that there are other embodiments of the invention that differ in details without affecting the essential nature thereof. Therefore the invention is not limited by that which is illustrated in the figure and described in the specification, but only as indicated in the accompanying claims, with the proper scope determined only by the broadest interpretation of said claims.

A better understanding of the features and advantages of the present disclosure will be obtained by reference to the following detailed description that sets forth illustrative embodiments, in which the principles of embodiments of the present disclosure are utilized, and the accompanying drawings.

The embodiments disclosed herein can be combined in one or more of many ways to provide improved spectrometer methods and apparatus.

As used herein like characters refer to like elements.

As used herein "light" encompasses electromagnetic radiation having wavelengths in one or more of the ultraviolet, visible, or infrared portions of the electromagnetic spectrum.

As used herein, the term "dispersive" is used, with respect to optical components, to describe a component that is designed to separate spatially, the different wavelength components of a polychromatic beam of light. Non-limiting examples of "dispersive" optical elements by this definition include diffraction gratings and prisms. The term specifically excludes elements such as lenses that disperse light because of non-idealities such as chromatic aberration or elements such as interference filters that have different transmission profiles according to the angle of incident radiation. The term also excludes the filters and filter matrixes described herein.

Figure 1:
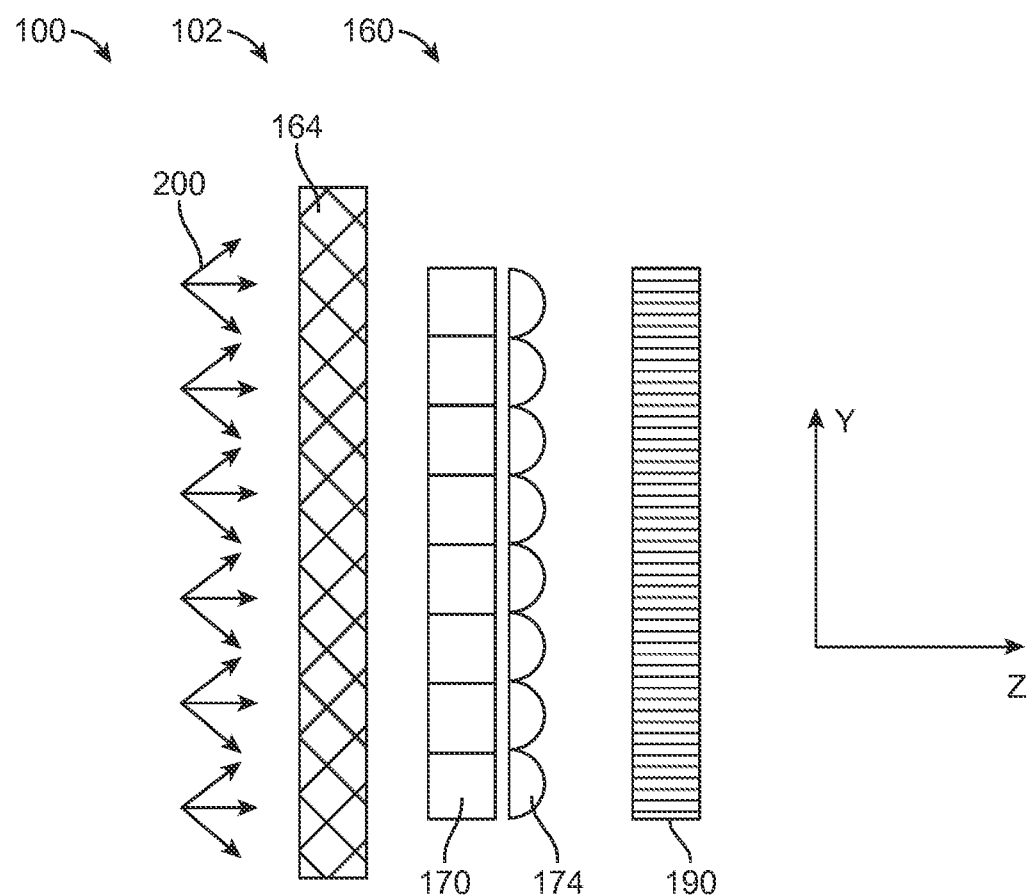
FIG. 1 shows schematic diagrams of the optical layout in accordance with embodiments.

Reference is now made to FIG. 1, which illustrates non-limiting embodiments of the compact spectrometer system 100 herein disclosed. As illustrated the system comprises a diffuser 164, a filter matrix 170, a lens array 174 and a detector 190.

In many embodiments, the spectrometer system comprises a plurality of optical filters of filter matrix 170. The optical filter can be of any type known in the art. Non-limiting examples of suitable optical filters include Fabry-Perot (FP) resonators, cascaded FP resonators, and interference filters. For example, a narrow bandpass filter (≤10 nm) with a wide blocking range outside of the transmission band (at least 200 nm) can be used. The center wavelength (CWL) of the filter can vary with the incident angle of the light impinging upon it.

In many embodiments, the central wavelength of the central band can vary by 10 nm or more, such that the effective range of wavelengths passed with the filter is greater than the bandwidth of the filter. In many embodiments, the central wavelength varies by an amount greater than the bandwidth of the filter. For example, the bandpass filter can have a bandwidth of no more than 10 nm and the wavelength of the central band can vary by more than 10 nm across the field of view of the sensor.

In many embodiments, the spectrometer system comprises detector 190, which may comprise an array of sensors. In many embodiments, the detector is capable of detecting light in the wavelength range of interest. The compact spectrometer system disclosed herein can be used from the UV to the IR, depending on the nature of the spectrum being obtained and the particular spectral properties of the sample being tested. In some embodiments, a detector that is capable of measuring intensity as a function of position (e.g. an array detector or a two-dimensional image sensor) is used.

In some embodiments the spectrometer does not comprise a cylindrical beam volume hologram (CVBH).

In many embodiments, the spectrometer system comprises a diffuser. In embodiments in which the light emanating from the sample is not sufficiently diffuse, a diffuser can be placed in front of other elements of the spectrometer. Collimated (or partially collimated light) can impinge on the diffuser, which then produces diffuse light which then impinges on other aspects of the spectrometer, e.g. an optical filter.

In many embodiments, the spectrometer system comprises a filter matrix. The filter matrix can comprise one or more filters, for example a plurality of filters. The filter matrix can comprise more than 2, 10, 50, or 100 filters (also referred to as sub-filters). The use of a single filter can limit the spectral range available to the spectrometer. For example, if the angle of incidence of light is larger than 30°, the system may not produce a signal of sufficient intensity due to lens aberrations and the decrease in the efficiency of the detector at large angles. For an angular range of 30° and an optical filter CWL of ~850 nm, the spectral range available to the spectrometer can be about 35 nm, for example. As this range can be insufficient for some spectroscopy based applications, embodiments with larger spectral ranges may comprise an optical filter matrix composed of a plurality of sub-filters. Each sub-filter can have a different CWL and thus covers a different part of the optical spectrum. The sub-filters can be configured in one or more of many ways and be tiled in two dimensions, for example.

Depending on the number of sub-filters, the wavelength range accessible to the spectrometer can reach hundreds of nanometers. In embodiments comprising a plurality of sub-filters, the approximate Fourier transforms formed at the image plane (i.e. one per sub-filter) overlap, and the signal obtained at any particular pixel of the detector can result from a mixture of the different Fourier transforms.

In some embodiments the filter matrix are arranged in a specific order to inhibit cross talk on the detector of light emerging from different filters and to minimize the effect of stray light. For example, if the matrix is composed of 3×4 filters then there are 2 filters located at the interior of the matrix and 10 filters at the periphery of the matrix. The 2 filters at the interior can be selected to be those at the edges of the wavelength range. Without being bound by a particular theory the selected inner filters may experience the most spatial cross-talk but be the least sensitive to cross-talk spectrally.

In many embodiments, the spectrometer system comprises detector 190. The detector can be sensitive to one or more of ultraviolet wavelengths of light, visible wavelengths of light, or infrared wavelengths of light.

The detector can be located in a predetermined plane. The predetermined plane can be the focal plane of the lens array. Light of different wavelengths (X1, X2, X3, X4, etc.) can arrive at the detector as a series of substantially concentric circles of different radii proportional to the wavelength. The relationship between the wavelength and the radius of the corresponding circle may not be linear.

The detector, in some embodiments, receives non-continuous spectra, for example spectra that can be unlike a dispersive element would create. The non-continuous spectra can be missing parts of the spectrum. The non-continuous spectrum can have the wavelengths of the spectra at least in part spatially out of order, for example. In some embodiments, first short wavelengths contact the detector near longer wavelengths, and second short wavelengths contact the detector at distances further away from the first short wavelengths than the longer wavelengths.

The detector may comprise a plurality of detector elements, such as pixels for example. Each detector element may be configured so as to receive signals of a broad spectral range. The spectral range received on the first and second pluralities of detector elements may extend at least from about 10 nm to about 400 nm. In many embodiments, spectral range received on the first and second pluralities of detector elements may extend at least from about 10 nm to about 700 nm. In many embodiments, spectral range received on the first and second pluralities of detector elements may extend at least from about 10 nm to about 1600 nm. In many embodiments, spectral range received on the first and second pluralities of detector elements may extend at least from about 400 nm to about 1600 nm. In many embodiments, spectral range received on the first and second pluralities of detector elements may extend at least from about 700 nm to about 1600 nm.

In many embodiments the lens array, the filter matrix, and the detector are not centered on a common optical axis. In many embodiments the lens array, the filter matrix, and the detector are aligned on a common optical axis.

In many embodiments, the principle of operation of compact spectrometer comprises one or more of the following attributes. Light impinges upon the diffuser. The light next impinges upon the filter matrix at a wide range of propagation angles and the spectrum of light passing through the sub-filters is angularly encoded. The angularly encoded light then passes through the lens array (e.g. Fourier transform focusing elements) which performs (approximately) a spatial Fourier transform of the angle-encoded light, transforming it into a spatially-encoded spectrum. Finally the light reaches the detector. The location of the detector element relative to the optical axis of a lens of the array corresponds to the wavelength of light, and the wavelength of light at a pixel location can be determined based on the location of the pixel relative to the optical axis of the lens of the array. The intensity of light recorded by the detector element such as a pixel as a function of position (e.g. pixel number or coordinate reference location) on the sensor corresponds to the resolved wavelengths of the light for that position.

In some embodiments, an additional filter is placed in front of the compact spectrometer system in order to block light outside of the spectral range of interest (i.e. to prevent unwanted light from reaching the detector).

In embodiments in which the spectral range covered by the optical filters is insufficient, additional sub-filters with differing CWLs can be used.

In some embodiments shutters allow for the inclusion or exclusion of light from part of the system. For example shutters can be used to exclude particular sub-filters. Shutters may also be used to exclude individual lens.

In some embodiments, the measurement of the sample is performed using scattered ambient light.

In many embodiments, the spectrometer system comprises a light source. The light source can be of any type (e.g. laser or light-emitting diode) known in the art appropriate for the spectral measurements to be made. In some embodiments the light source emits from 350 nm to 1100 nm. The wavelength(s) and intensity of the light source will depend on the particular use to which the spectrometer will be put. In some embodiments the light source emits from 0.1 mW to 500 mW Because of its small size and low complexity, the compact spectrometer system herein disclosed can be integrated into a mobile communication device such as a cellular telephone. It can either be enclosed within the device itself, or mounted on the device and connected to it by wired or wireless means for providing power and a data link. By incorporating the spectrometer system into a mobile device, the spectra obtained can be uploaded to a remote location, analysis can be performed there, and the user notified of the results of the analysis. The spectrometer system can also be equipped with a GPS device and/or altimeter so that the location of the sample being measured can be reported. Further non-limiting examples of such components include a camera for recording the visual impression of the sample and sensors for measuring such environmental variables as temperature and humidity.

Because of its small size and low cost, the spectrometer system herein disclosed can also be integrated into kitchen appliances such as ovens (e.g. microwave ovens), food processors, toilets refrigerators etc. The user can then make a determination of the safety of the ingredients in real time during the course of food storage and preparation.

In many embodiments, the spectrometer also includes a power source (e.g. a battery or power supply). In some embodiments the spectrometer is powered by a power supply from a consumer hand held device (e.g. a cell phone). In some embodiments the spectrometer has an independent power supply. In some embodiments a power supply from the spectrometer can supply power to a consumer hand held device.

In many embodiments, the spectrometer comprises a processing and control unit. In some embodiments the spectrometer does not analyze the data collected, and the spectrometer relays data to a remote processing and control unit, such as a back end server. Alternatively or in combination, the spectrometer may partially analyze the data prior to transmission to the remote processing and control unit. The remote processing and control unit can be coupled to the spectrometer with a consumer hand held device (e.g. a cell phone). The remote processing and control unit can be a cloud based system which can transmit analyzed data or results to a user. In some embodiments a hand held device is configured to receive analyzed data and can be associated with the spectrometer. The association can be through a physical connection or wireless communication, for example.

The spectrometers as described herein can be adapted, with proper choice of light source, detector, and associated optics, for a use with a wide variety of spectroscopic techniques.

Non-limiting examples include Raman, fluorescence, and IR or UV-VIS reflectance and absorbance spectroscopies. Because, as described above, compact spectrometer system can separate a Raman signal from a fluorescence signal, in some embodiments of the invention, the same spectrometer is used for both spectroscopies.

In some embodiments the spectrometer system comes equipped with a memory with a database of spectral data stored therein and a microprocessor with analysis software programmed with instructions. In some embodiments the spectrometer system is in communication with a computer memory having a database of spectral data stored therein and a microprocessor with analysis software programmed in. The memory can be volatile or non-volatile in order to store the user's own measurements in the memory. The database and/or all or part of the analysis software can stored remotely, and the spectrometer system can communicate with the remote memory via a network (e.g. a wireless network) by any appropriate method. Alternatively, the database of spectral data can be provided with a computer located near the spectrometer, for example in the same room.

In some embodiments in which the database is located remotely, the data base can be updated often at regular intervals, for example continuously. In these embodiments, each measurement made by a user of the spectrometer increases the quality and reliability of future measurements made by any user.

Once a spectrum is then obtained it can be analyzed. In some embodiments the analysis is not contemporaneous. In some embodiments the analysis is in real time. The spectrum can be analyzed using any appropriate analysis method. Non-limiting examples of spectral analysis techniques that can be used include Principal Components Analysis, Partial Least Squares analysis, and the use of a neural network algorithm to determine the spectral components.

An analyzed spectrum can determine whether a complex mixture being investigated contains a spectrum associated with components. The components can be, e.g., a substance, mixture of substances, or microorganisms.

The intensity of these components in the spectrum can be used to determine whether a component is at a certain concentration, e.g. whether their concentration of an undesirable component is high enough to be of concern. Non-limiting examples of such substances include toxins, decomposition products, or harmful microorganisms. In some embodiments of the invention, if it is deemed likely that the sample is not fit for consumption, the user is provided with a warning.

In some embodiments, the spectrometer is connected to a communication network that allows users to share the information obtained in a particular measurement. An updatable database located in the "cloud" (i.e. the distributed network) constantly receives the results of measurements made by individual users and updates itself in real time, thus enabling each successive measurement to be made with greater accuracy and confidence as well as expanding the number of substances for which a spectral signature is available.

In various embodiments of the invention, the conversion of the raw intensity data to a spectrum may be performed either locally (with a processor and software supplied with the spectrometer system) or remotely. Heavier calculations for more complicated analyses for example can be performed remotely.

In embodiments that incorporate remote data analysis, the data transferred to the remote system may include one or more of raw detector data; pre-processed detector data or post-processed detector data in which the processing was performed locally; or the spectrum derived from the raw detector data.

In some embodiments the spectrometer does not comprise a monochromator.

In some embodiments of the invention, the following signal processing scheme is used. First, an image or a series of images is captured by the image sensor in the spectrometer mentioned above. The images are analyzed by a local processing unit. This stage of analysis may include any or all of image averaging, compensation for aberrations of the optical unit, reduction of detector noise by use of a noise reduction algorithm, or conversion of the image into a raw spectrum. The raw spectrum is then transmitted to a remote processing unit; in preferred embodiments, the transmission is performed using wireless communication.

The raw spectrum can be analyzed remotely. Noise reduction can be performed remotely.

In embodiments in which a Raman spectrum is obtained, the Raman signal can be separated from any fluorescence signal. Both Raman and fluorescence spectra can be compared to existing calibration spectra. After a calibration is performed, the spectra can be analyzed using any appropriate algorithm for spectral decomposition; non-limiting examples of such algorithms include Principal Components Analysis, Partial Least-Squares analysis, and spectral analysis using a neural network algorithm. This analysis provides the information needed to characterize the sample that was tested using the spectrometer. The results of the analysis are then presented to the user.

Figure 2:
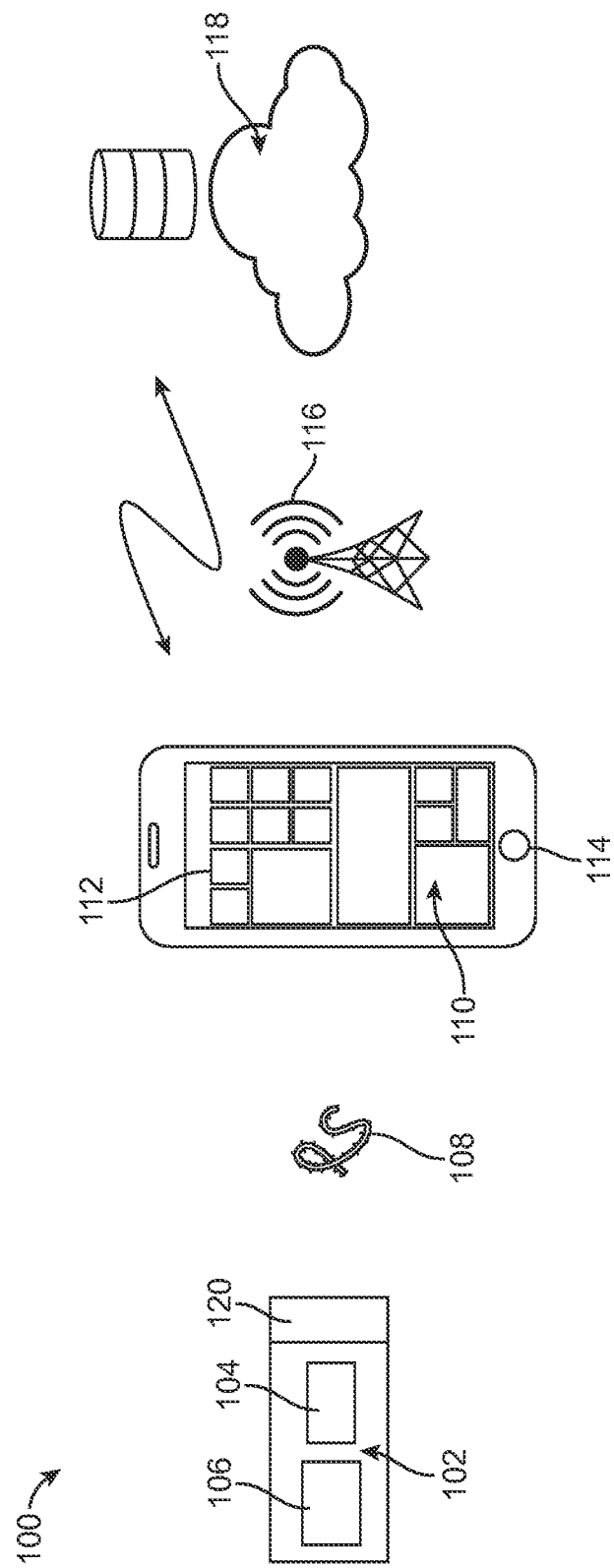
FIG. 2 shows a schematic diagram of a spectrometer system, in accordance with embodiments.

FIG. 2 shows a schematic diagram of a spectrometer system according to embodiments. In many embodiments, the spectrometer system 100 comprises a spectrometer 102 and a consumer hand held device 110 in wireless communication 116 with a cloud based storage system 118. The spectrometer 102 can acquire the data as described herein. The hand held spectrometer 102 may comprise a processor 106 and communication circuitry 104 coupled to spectrometer head 120 having spectrometer components as described herein. The spectrometer can transmit the data to the handheld device 110 with communication circuitry 104 with a communication link, such as a wireless serial communication link, for example Bluetooth™. The hand held device can receive the data from the spectrometer 102 and transmit the data to a back end server of the cloud based storage system 118.

The hand held device 110 may comprise one or more components of a smart phone, such as a display 112, an interface 114, a processor, a computer readable memory and communication circuitry. The device 110 may comprise a substantially stationary device when used, such as a wireless communication gateway, for example.

The processor 106 may comprise a tangible medium embodying instructions, such as a computer readable memory embodying instructions of a computer program. Alternatively or in combination the processor may comprise logic such as gate array logic in order to perform one or more logic steps.

Figure 3:
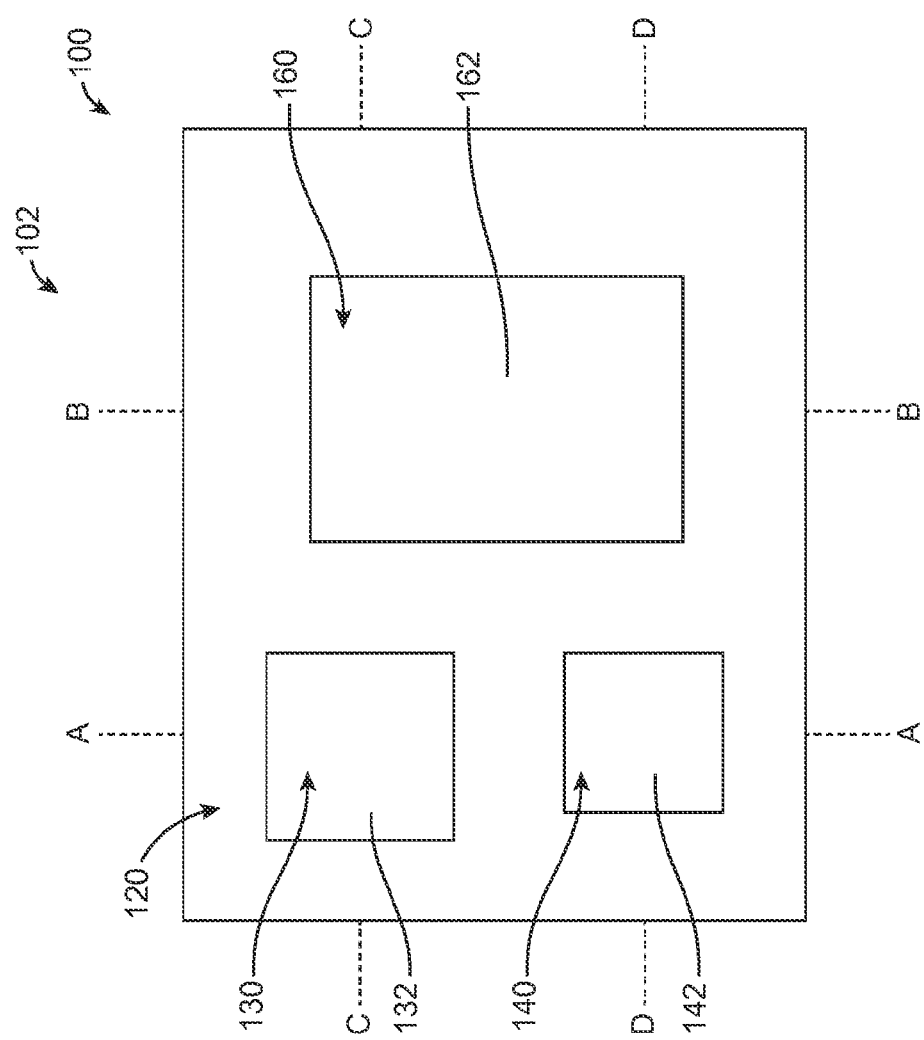
FIG. 3 shows a schematic diagram of a spectrometer head, in accordance with embodiments.

FIG. 3 shows a schematic diagram of spectrometer head in accordance with embodiments. In many embodiments, the spectrometer 102 comprises a spectrometer head 120. The spectrometer head comprises one or more of a spectrometer module 160, a temperature sensor module 130, and an illumination module 140. Each module, when present, can be covered with a module window. For example, the spectrometer module 160 can comprise a spectrometer window 162, the temperature sensor module 130 can comprise a temperature sensor window 132, and the illumination module 140 can comprise an illumination window 142.

In many embodiments, the illumination module and the spectrometer module are configured to have overlapping fields of view at the sample. The overlapping fields of view can be provided in one or more of many ways. For example, the optical axes of the illumination source, the temperature sensor and the matrix array can extend in a substantially parallel configuration. Alternatively, one or more of the optical axes can be oriented toward another optical axis of another module.

Figure 4:
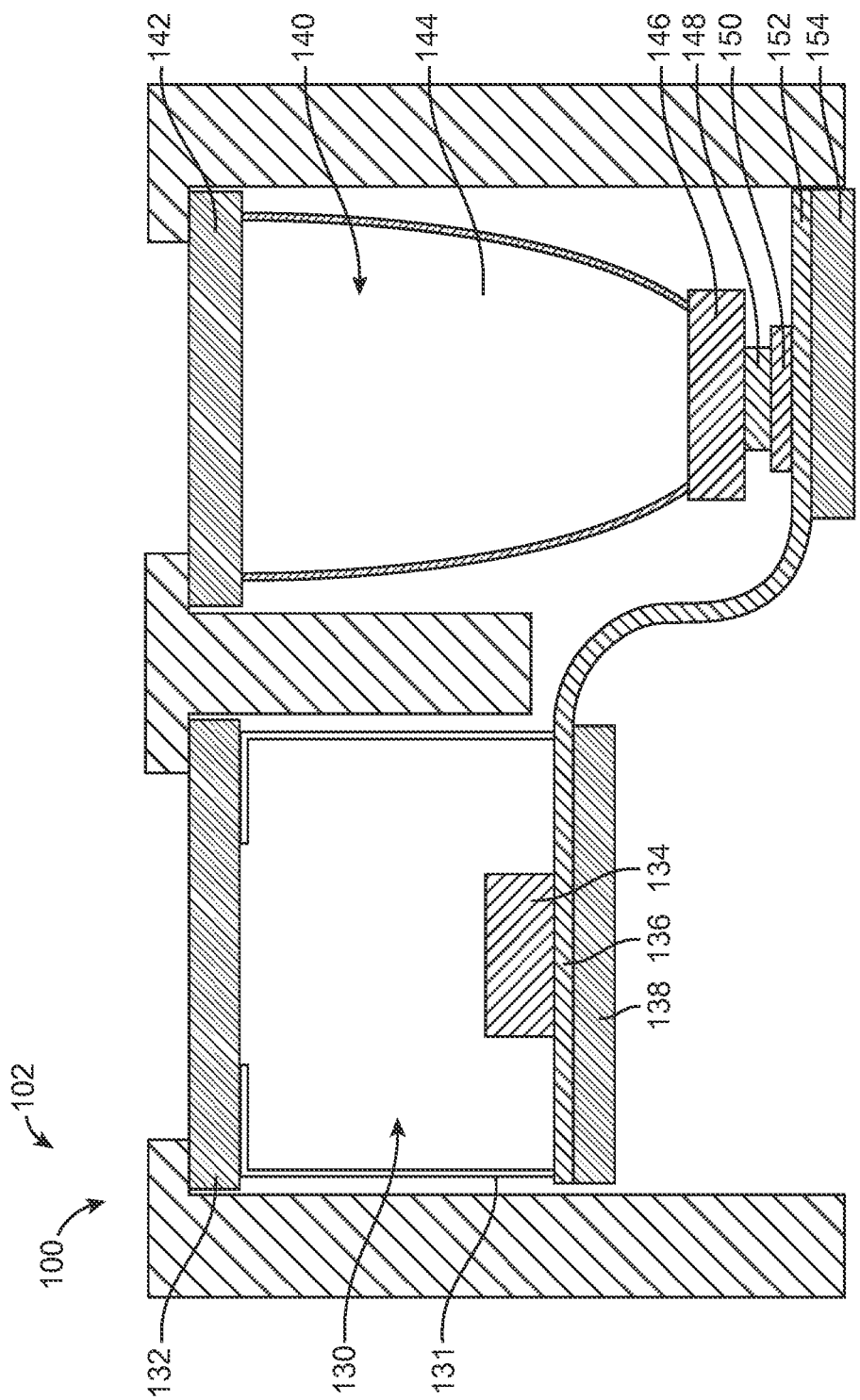
FIG. 4 shows a schematic diagram of cross-section A of the spectrometer head of FIG. 3, in accordance with embodiments.

FIG. 4 shows a schematic drawing of cross-section A of the spectrometer head of FIG. 3, in accordance with embodiments. In order to lessen the noise and/or spectral shift produced from fluctuations in temperature, a spectrometer head 102 comprising temperature sensor module 130 can be used to measure and record the temperature during the measurement. In some embodiments, the temperature sensor element can measure the temperature of the sample in response to infrared radiation emitted from the sample, and transmit the temperature measurement to a processor. Accurate and/or precise temperature measurement can be used to standardize or modify the spectrum produced. For example, different spectra of a given sample can be measured based on the temperature at which the spectrum was taken. In some embodiments, a spectrum can be stored with metadata relating to the temperature at which the spectrum was measure. In many embodiments, the temperature sensor module 130 comprises a temperature sensor window 132. The temperature sensor window can seal the sensor module. The temperature sensor window 132 can be made of material that is substantially non-transmissive to visible light and transmits light in the infrared spectrum. In some embodiments the temperature sensor window 132 comprises germanium, for example. In some embodiments, the temperature sensor window is about 0.2, 0.3, 0.4, 0.5, 0.6, 0.7, 0.8, 0.9 or 1.0 mm thick.

The temperature sensor can comprise a field of view (herein after "FoV") limiter. In many embodiments, the temperature sensor has a field of view oriented to overlap with a field of view of the detector and a field of view of an illuminator. For example, the field of view can be limited by an aperture formed in a material supporting the window 132 of temperature sensor module and the dimensions of the temperature sensor 134. In some embodiments, the temperature sensor module has a limited field of view and comprises a heat conductive metal cage disposed on a flex printed circuit board (PCB) 136. The PCB 136 can be mounted on a stiffener 138 in order to inhibit movement relative to the other modules on the sensor head. In some embodiments, the flexible circuit board is backed by stiffener 138 comprising a metal. The temperature sensor 134 can be a remote temperature sensor. In some embodiments, the temperature sensor can give a temperature that is accurate to within about 5, 4, 3, 2, 1, 0.7, 0.4, 0.3, 0.2 or 0.1 degree Celsius of the ambient temperature of the sample. In some embodiments, the temperature sensor measures the ambient temperature with precision to 3, 2, 1, 0.5, or 0.1 degree Celsius.

In many embodiments, the spectrometer head comprises illumination module 140. The illumination module can illuminate a sample with light. In some embodiments, the illumination module comprises an illumination window 142. The illumination window can seal the illumination module. The illumination window can be substantially transmissive to the light produced in the illumination module. For example, the illumination window can comprise glass. The illumination module can comprise a light source 148. In some embodiments, the light source can comprise one or more light emitting diodes (LED). In some embodiments, the light source comprises a blue LED. In some embodiments, the light source comprises a red or green LED or an infrared LED.

The light source 148 can be mounted on a mounting fixture 150. In some embodiments, the mounting fixture comprises a ceramic package. For example, the light fixture can be a flip-chip LED die mounted on a ceramic package. The mounting fixture 150 can be attached to a flexible printed circuit board (PCB) 152 which can optionally be mounted on a stiffener 154 to reduce movement of the illumination module. The flex PCB of the illumination module and the PCT of temperature sensor modules may comprise different portions of the same flex PCB, which may also comprise portions of spectrometer PCB.

The wavelength of the light produced by the light source 148 can be shifted by a plate 146. Plate 146 can be a wavelength shifting plate. In some embodiments, plate 146 comprises phosphor embedded in glass. Alternatively or in combination, plate 146 can comprise a nano-crystal, a quantum dot, or combinations thereof. The plate can absorb light from the light source and release light having a frequency lower than the frequency of the absorbed light. In some embodiments, a light source produces visible light, and plate 146 absorbs the light and emits near infrared light. In some embodiments, the light source is in close proximity to or directly touches the plate 146. In some embodiments, the light source and associated packaging is separated from the plate by a gap to limit heat transfer. For example the gap between the light source and the plate can be at least 0.1, 0.2, 0.3, 0.4, 0.5, 0.6, 0.7, 0.8, 0.9, 1.0, 1.5, 2.0, 2.5, 3.0, 3.5, 4.0, 5.0, 6.0, 7.0, 8.0, 9.0, or 10.0 mm. In many alternative embodiments, the light source packaging touches the plate 146 in order to conduct heat from the plate such that the light source packaging comprises a heat sink.

The illumination module can further comprise a light concentrator such as a parabolic concentrator 144 or a condenser lens in order to concentrate the light. In some embodiments, the parabolic concentrator 144 is a reflector. In some embodiments, the parabolic concentrator 144 comprises stainless steel. In some embodiments, the parabolic concentrator 144 comprises gold-plated stainless steel. In some embodiments, the concentrator can concentrate light to a cone. For example, the light can be concentrated to a cone with a field of view of about 30-45, 25-50, or 20-55 degrees.

In some embodiments, the illumination module is configured to transmit light and the spectrometer module is configured to receive light along optical paths extending substantially perpendicular to an entrance face of the spectrometer head. In some embodiments, the modules can be configured to such that light can be transmitted from one module to an object (such as a sample 108) and reflected or scattered to another module which receives the light.

In some embodiments, the optical axes of the illumination module and the spectrometer module are configured to be non-parallel such that the optical axis representing the spectrometer module is at an offset angle to the optical axis of the illumination module. This non-parallel configuration can be provided in one or more of many ways. For example, one or more components can be supported on a common support and offset in relation to an optic such as a lens in order to orient one or more optical axes toward each other. Alternatively or in combination, a module can be angularly inclined with respect to another module. In some embodiments, the optical axis of each module is aligned at an offset angle of greater than 1, 2, 3, 4, 5, 6, 7, 8, 9, 10, 12, 14, 16, 18, 20, 25, 30, 35, 40, 45, or 50 degrees. In some embodiments, the illumination module and the spectrometer module are configured to be aligned at an offset angle of less than 1, 2, 3, 4, 5, 6, 7, 8, 9, 10, 12, 14, 16, 18, 20, 25, 30, 35, 40, 45, or 50 degrees. In some embodiments, the illumination module and the spectrometer module are configured to be aligned at an offset angle between than 1-10, 11-20, 21-30, 31-40 or 41-50 degrees. In some embodiments, the offset angle of the modules is set firmly and is not adjustable. In some embodiments, the offset angle of the modules is adjustable. In some embodiments, the offset angle of the modules is automatically selected based on the distance of the spectrometer head from the sample. In some embodiments, two modules have parallel optical axes. In some embodiments, two or more modules have offset optical axes. In some embodiments, the modules can have optical axes offset such that they converge on a sample. The modules can have optical axes offset such that they converge at a set distance. For example, the modules can have optical axes offset such that they converge at a distance of about 10, 20, 30, 40, 50, 60, 70, 80, 90, 100, 150, 200, 250, 300, 350, 400, or 500 mm away.

Figure 5:
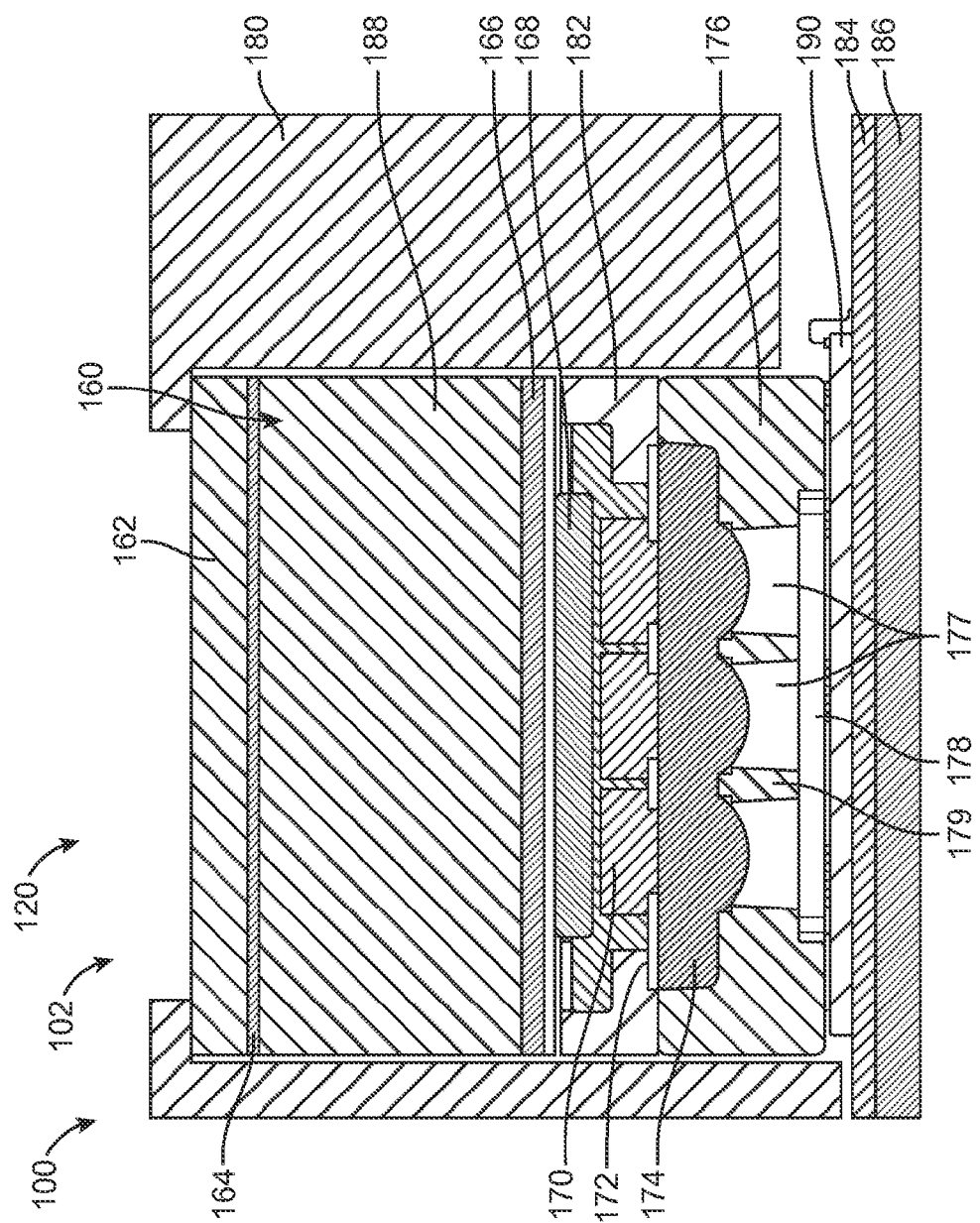
FIG. 5 shows a schematic diagram of cross-section B of the spectrometer head of FIG. 3, accordance with embodiments.

FIG. 5 shows a schematic drawing of cross-section B of the spectrometer head of FIGS. 3 and 4, in accordance with embodiments. In many embodiments, the spectrometer head 102 comprises spectrometer module 160. The spectrometer module can be sealed by a spectrometer window 162. In some embodiments, the spectrometer window 162 is selectively transmissive to light with respect to the wavelength in order to analyze the spectral sample. For example, spectrometer window 162 can be an IR-pass filter. In some embodiments, window 162 can be glass. The spectrometer module can comprise one or more diffusers. For example, the spectrometer module can comprise a first diffuser 164 disposed below the spectrometer window 162. The first diffuser 164 can distribute the incoming light. For example, the first diffuser can be a cosine diffuser. Optionally, the spectrometer module comprises a light filter 188. Light filter 188 can be a thick IR-pass filter. For example, filter 188 can absorb light below a threshold wavelength. In some embodiments, filter 188 absorbs light with a wavelength below about 1000, 950, 900, 850, 800, 750, 700, 650, or 600 nm. In some embodiments, the spectrometer module comprises a second diffuser 166. The second diffuser can generate lambertian light distribution at the input of the filter matrix 170. The filter assembly can be sealed by a glass plate 168. Alternatively or in combination, the filter assembly can be further supported a filter frame 182, which can attach the filter assembly to the spectrometer housing 180. The spectrometer housing 180 can hold the spectrometer window 162 in place and further provide mechanical stability to the module.

The first filter and the second filter can be arranged in one or more of many ways to provide a substantially uniform light distribution to the filters. The substantially uniform light distribution can be uniform with respect to an average energy to within about 25%, for example to within about 10%, for example. In many embodiments the first diffuser distributes the incident light energy spatially on the second diffuser with a substantially uniform energy distribution profile. In some embodiments, the first diffuser makes the light substantially homogenous with respect to angular distribution. The second diffuser further diffuses the light energy of the substantially uniform energy distribution profile to a substantially uniform angular distribution profile, such that the light transmitted to each filter can be substantially homogenous both with respect to the spatial distribution profile and the angular distribution profile of the light energy incident on each filter. For example, the angular distribution profile of light energy onto each filter can be uniform to within about +/−25%, for example substantially uniform to within about +/−10%.

In many embodiments, the spectrometer module comprises a filter matrix 170. The filter matrix can comprise one or more filters. In many embodiments, the filter matrix comprises a plurality of filters. For example, the filter matrix can comprise filters arranged in a square, rectangle, circle, oval, or disordered arrangement of filters. The filter array can comprise at least 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 200 or more filters. In some embodiments, the filter matrix comprises between 1 and 36 inclusive filters arranged in a square or rectangular arrangement selected from the group consisting of 1×1, 1×2, 2×2, 3×1, 2×3, 3×3, 4×1, 4×2, 4×3, 4×4, 5×1, 5×2, 5×3, 5×4, 5×5, 6×1, 6×2, 6×3, 6×4, 6×5 or 6×6. In some embodiments, the filter array comprises between about 10 and about 100 filters. In some embodiments, the filter array comprises between about 10 and about 30 filters. In some embodiments, the filter array comprises 4 rows filters wherein each row comprises 3 filters.

In some embodiments, each filter of the filter matrix 170 is configured to transmit a range of wavelengths distributed about a central wavelength. The range of wavelengths can be defined as a full width half maximum (hereinafter "FWHM") of the distribution of transmitted wavelengths for a light beam transmitted substantially normal to the surface of the filter as will be understood by a person of ordinary skill in the art. A wavelength range can be defined by a central wavelength and by a spectral width. The central wavelength can be the mean wavelength of light transmitted through the filter, and the band spectral width of a filter can be the difference between the maximum and the minimum wavelength of light transmitted through the filter. For example, a filter can have a central wavelength of 300 nm and a wavelength range of 20 nm which would transmit light having a wavelength from 290 to 310 nm, and the filter would substantially not transmit light below 290 nm or above 310 nm. In some embodiments, each filter of the plurality of filters is configured to transmit a range of wavelengths different from other filters of the plurality. In some embodiments, the range of wavelengths overlaps with ranges of said other filters of the plurality and wherein said each filter comprises a central wavelength different from said other filters of the plurality. In some embodiments, the spectral width of each filter is less than 200, 190, 180, 170, 160, 150, 140, 130, 120, 110, 100, 90, 80, 70, 60, 50, 40, 30, 20, 18, 16, 14, 12, 10, 8, 6, 4, 3, 2, or 1 nm. In some embodiments, the spectral width of each filter is at least 1, 2, 4, 6, 8, 10, 12, 14, 16, 18, 20, 30, 40, 50, 60, 70, 80, 90, or 100 nm. In some embodiments, the spectral width of each filter is between about 1 to about 60 nm, about 2 to about 50 nm, from about 4 to about 40 nm, or from about 8 to about 30 nm. In some embodiments, the central wavelengths of each filter at least 1, 2, 3, 4, 5, 6, 7, 8, 9, 10, 11, 12, 14, 16, 18, 20, 25, 30, 35, 40, 50, 60, 70, 80, 90, 100, or 200 nm from the central wavelength of each other filter.

In many embodiments, the filter array comprises a substrate having a thickness and a first side and a second side, the first side oriented toward the diffuser, the second side oriented toward the lens array. In some embodiments, each filter of the filter array comprises a substrate having a thickness and a first side and a second side, the first side oriented toward the diffuser, the second side oriented toward the lens array. The filter array can comprise one or more coatings on the first side, on the second side, or a combination thereof. Each filter of the filter array can comprise one or more coatings on the first side, on the second side, or a combination thereof. In some embodiments, each filter of the filter array comprises one or more coatings on the second side, oriented toward the lens array. In some embodiments, each filter of the filter array comprises one or more coatings on the second side, oriented toward the lens array and on the first side, oriented toward the diffuser. The one or more coatings on the second side can be an optical filter. For example, the one or more coatings can permit a wavelength range to selectively pass through the filter. Alternatively or in combination, the one or more coatings can be used to inhibit cross-talk among lenses of the array. In some embodiments, the plurality of coatings on the second side comprises a plurality of interference filters, said each of the plurality of interference filters on the second side configured to transmit a central wavelength of light to one lens of the plurality of lenses. In some embodiments, the filter array comprises one or more coatings on the first side of the filter array. The one or more coatings on the first side of the array can comprise a coating to balance mechanical stress. In some embodiments, the one or more coatings on the first side of the filter array comprises an optical filter. For example, the optical filter on the first side of the filter array can comprise an IR pass filter to selectively pass infrared light. In many embodiments, the first side does not comprise a bandpass interference filter coating. In some embodiments, the first does not comprise a coating.

In many embodiments, the array of filters comprises a plurality of bandpass interference filters on the second side of the array. The placement of the fine frequency resolving filters on the second side oriented toward the lens array and apertures can inhibit cross-talk among the filters and related noise among the filters. In many embodiments, the array of filters comprises a plurality of bandpass interference filters on the second side of the array, and does not comprise a bandpass interference filter on the first side of the array.

In many embodiments, each filter defines an optical channel of the spectrometer. The optical channel can extend from the filer through an aperture and a lens of the array to a region of the sensor array. The plurality of parallel optical channels can provide increased resolution with decreased optical path length.

The spectrometer module can comprise an aperture array 172. The aperture array can prevent cross talk between the filters. The aperture array comprises a plurality of apertures formed in a non-optically transmissive material. In some embodiments, the plurality of apertures is dimensioned to define a clear lens aperture of each lens of the array, wherein the clear lens aperture of each lens is limited to one filter of the array. In some embodiments, the clear lens aperture of each lens is limited to one filter of the array.

In many embodiments the spectrometer module comprises a lens array 174. The lens array can comprise a plurality of lenses. The number of lenses can be determined such that each filter of the filter array corresponds to a lens of the lens array. Alternatively or in combination, the number of lenses can be determined such that each channel through the support array corresponds to a lens of the lens array. Alternatively or in combination, the number of lenses can be selected such that each region of the plurality of regions of the image sensor corresponds to an optical channel and corresponding lens of the lens array and filter of the filter array.

In many embodiments, each lens of the lens array comprises one or more aspheric surfaces, such that each lens of the lens array comprises an aspherical lens. In many embodiments, each lens of the lens array comprises two aspheric surfaces. Alternatively or in combination, one or more individual lens of the lens array can have two curved optical surfaces wherein both optical surfaces are substantially convex. Alternatively or in combination, the lenses of the lens array may comprise one or more diffractive optical surfaces.

In many embodiments, the spectrometer module comprises a support array 176. The support array 176 comprises a plurality of channels 177 defined with a plurality of support structures 179 such as interconnecting annuli. The plurality of channels 177 may define optical channels of the spectrometer. The support structures 179 can comprises stiffness to add rigidity to the support array 176. The support array may comprise a stopper to limit movement and fix the position the lens array in relation to the sensor array. The support array 176 can be configured to support the lens array 174 and fix the distance from the lens array to the sensor array in order to fix the distance between the lens array and the sensor array at the focal length of the lenses of the lens array. In many embodiments, the lenses of the array comprise substantially the same focal length such that the lens array and the sensor array are arranged in a substantially parallel configuration.

The support array 176 can extend between the lens array 174 and the stopper mounting 178. The support array 176 can serve one or more purposes, such as 1) providing the correct separation distance between each lens of lens array 170 and each region of the plurality of regions of the image sensor 190, and/or 2) preventing stray light from entering or exiting each channel, for example. In some embodiments, the height of each support in support array 176 is calibrated to the focal length of the lens within lens array 174 that it supports. In some embodiments, the support array 176 is constructed from a material that does not permit light to pass such as substantially opaque plastic. In some embodiments, support array 176 is black, or comprises a black coating to further reduce cross talk between channels. The spectrometer module can further comprise a stopper mounting 178 to support the support array. In many embodiments, the support array comprises an absorbing and/or diffusive material to reduce stray light, for example.

In many embodiments, the support array 176 comprises a plurality of channels having the optical channels of the filters and lenses extending therethrough. In some embodiments, the support array comprise a single piece of material extending from the lens array to the detector (i.e. CCD or CMOS array).

The lens array can be directly attached to the aperture array 172, or can be separated by an air gap of at least 1, 2, 3, 4, 5, 6, 7, 8, 9, 10, 12, 14, 16, 18, 20, 30, 40, or 50 micrometers. The lens array can be directly on top of the support array 178. Alternatively or in combination, the lens array can be positioned such that each lens is substantially aligned with a single support stopper or a single optical isolator in order to isolate the optical channels and inhibit cross-talk. In some embodiments, the lens array is positioned to be at a distance approximately equal to the focal length of the lens away from the image sensor, such that light coming from each lens is substantially focused on the image sensor.

In some embodiments, the spectrometer module comprises an image sensor 190. The image sensor can be a light detector. For example, the image sensor can be a CCD or 2D CMOS or other sensor, for example. The detector can comprise a plurality of regions, each region of said plurality of regions comprising multiple sensors. For example, a detector can be made up of multiple regions, wherein each region is a set of pixels of a 2D CMOS. The detector, or image sensor 190, can be positioned such that each region of the plurality of regions is directly beneath a different channel of support array 176. In many embodiments, an isolated light path is established from a single of filter of filter array 170 to a single aperture of aperture array 172 to a single lens of lens array 174 to a single stopper channel of support array 176 to a single region of the plurality of regions of image sensor 190. Similarly, a parallel light path can be established for each filter of the filter array 170, such that there are an equal number of parallel (non-intersecting) light paths as there are filters in filter array 170.

The image sensor 190 can be mounted on a flexible printed circuit board (PCB) 184. The PCB 184 can be attached to a stiffener 186. In some embodiments, the stiffener comprises a metal stiffener to prevent motion of the spectrometer module relative to the spectrometer head 120.

Figure 6:
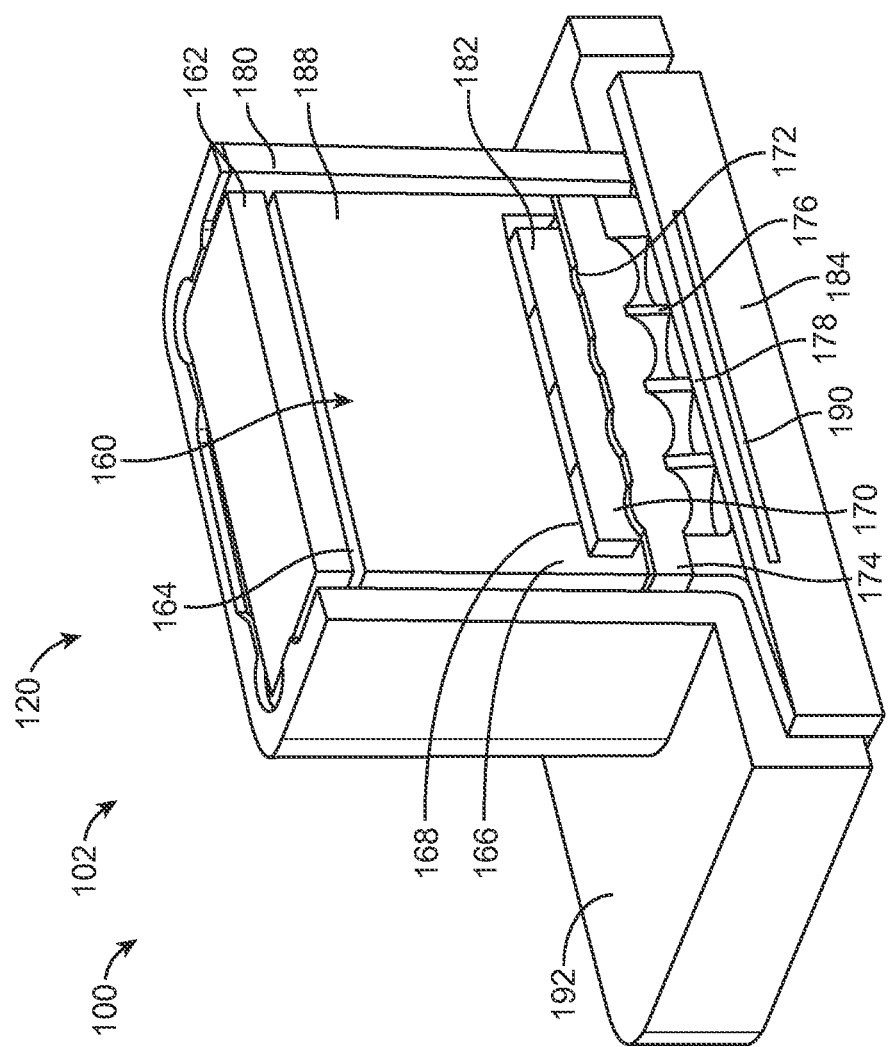
FIG. 6 shows a schematic diagram of a spectrometer module, in accordance with embodiments.

FIG. 6 shows an isometric view of a spectrometer module 160 in accordance with embodiments. The spectrometer module 160 comprises many components as described herein. In many embodiments, the support array 176 can be positioned on a package on top of the sensor. In many embodiments, the support array can be positioned over the top of the bare die of the sensor array such that an air gap is present. The air gap can be less than 10, 9, 8, 7, 6, 5, 4, 3, 2 or 1 micrometer(s).

Figure 7:
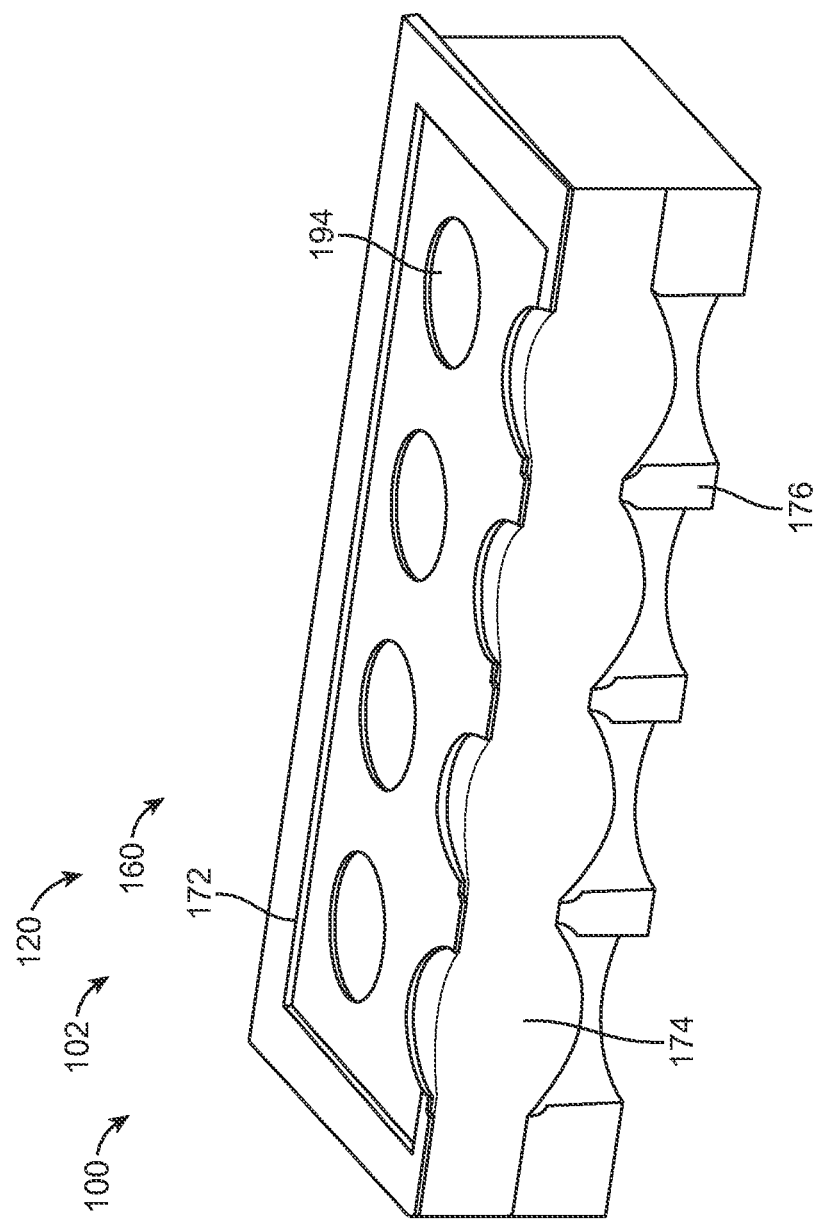
FIG. 7 shows a schematic diagram of apertures formed in a non-transmissive material and a lens array, in accordance with embodiments.

FIG. 7 shows the lens array 174 within the spectrometer module 160, in accordance with embodiments. This isometric view shows the apertures 194 formed in a non-transmissive material of the aperture array 172 in accordance with embodiments. In many embodiments, each channel of the support array 176 is aligned with a filter of the filter array 170, a lens of the lens array 174, and an aperture 194 of the aperture array in order to form a plurality of light paths with inhibited cross talk.

Figure 8:
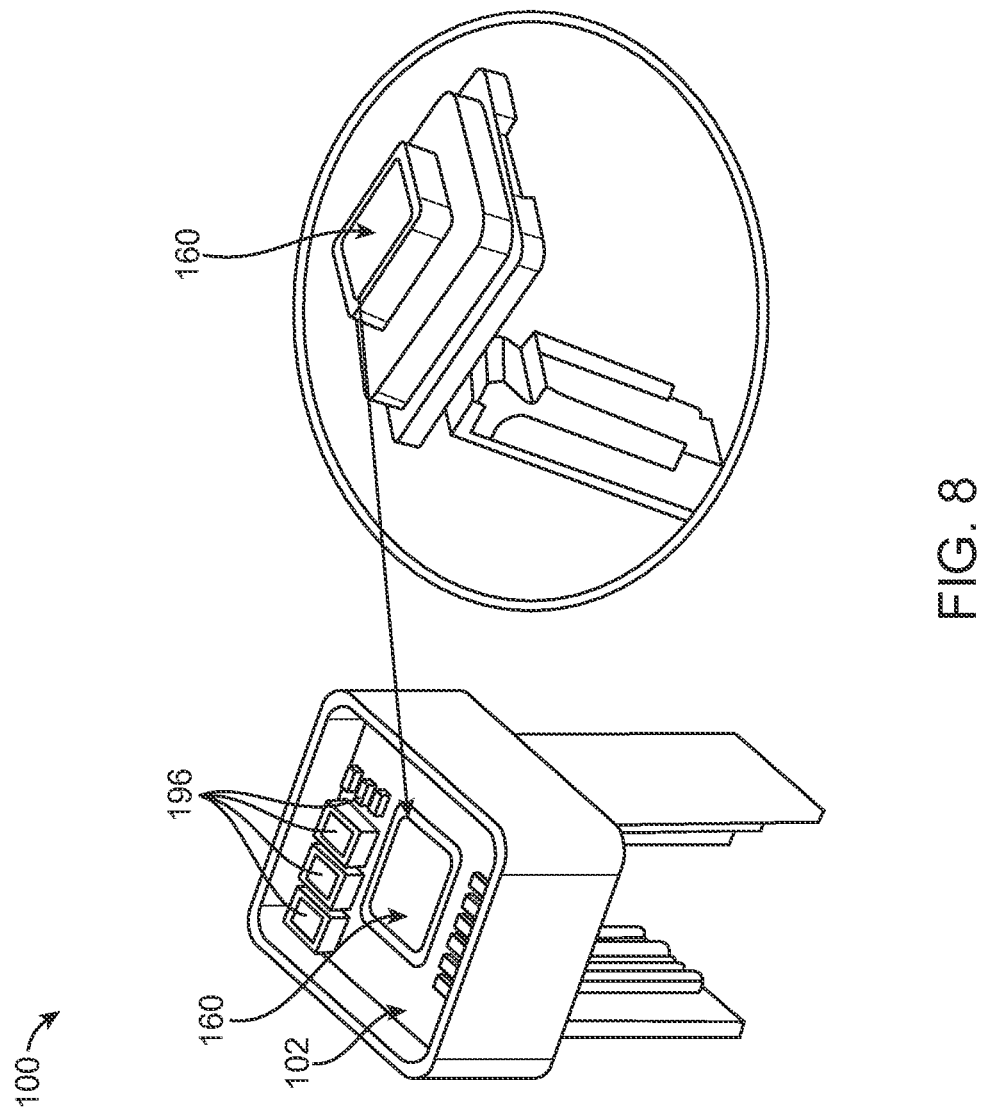
FIG. 8 shows a schematic diagram of a spectrometer, in accordance with embodiments.

FIG. 8 shows a spectrometer 102 in accordance with embodiments. The spectrometer can comprise an optical head which can comprise a spectrometer module 160. The spectrometer can further comprise a temperature sensor module. In many embodiments, the spectrometer comprises an illumination module. In many embodiments, the spectrometer comprises light emitting diodes 196 distinct from an illumination module. The spectrometer can also comprise further components such as a Bluetooth™ module to communicate data to another device, a spectrometer processor 106, a power supply, or combinations thereof.

Although the detailed description contains many specifics, these should not be construed as limiting the scope of the disclosure but merely as illustrating different examples and aspects of the present disclosure. It should be appreciated that the scope of the disclosure includes other embodiments not discussed in detail above. Various other modifications, changes and variations which will be apparent to those skilled in the art may be made in the arrangement, operation and details of the method and apparatus of the present disclosure provided herein without departing from the spirit and scope of the invention as described herein.

As used herein like characters identify like elements.

While preferred embodiments of the present disclosure have been shown and described herein, it will be obvious to those skilled in the art that such embodiments are provided by way of example only. Numerous variations, changes, and substitutions will be apparent to those skilled in the art without departing from the scope of the present disclosure. It should be understood that various alternatives to the embodiments of the present disclosure described herein may be employed without departing from the scope of the present invention. Therefore, the scope of the present invention shall be defined solely by the scope of the appended claims and the equivalents thereof.

What is claimed is:

1. A spectrometer comprising: a light path, the light path passing sequentially through a diffuser, a filter matrix, and a lens array; and
   at least one opaque aperture array between the filter matrix and the lens array;
   wherein the light path ends at a detector;
   wherein the detector comprises multiple sensors;
   wherein the light path from the diffuser to the detector is less than 9 mm
   and wherein the resolution of the spectrometer is less than 10 nm.

2. The spectrometer of claim 1 wherein the light path beginning at the diffuser and ending at the detector is less than 6 mm.

3. The spectrometer of claim 1 wherein the light path beginning at the diffuser and ending at the detector is less than 4.5 mm.

4. The spectrometer of claim 1 wherein the resolution of the spectrometer is less than 8 nm.

5. The spectrometer of claim 1 wherein the resolution of the spectrometer is less than 5 nm.

6. The spectrometer of claim 1 with a detectable wavelength range larger than 100 nm.

7. The spectrometer of claim 1 with a detectable wavelength range larger than 200 nm.

8. The spectrometer of claim 1 with a detectable wavelength range larger than 300 nm.

9. The spectrometer of claim 1 wherein the spectrometer does not comprise a dispersive optical element.

10. The spectrometer of claim 1 wherein the transmission spectra of the filters in the filter matrix vary with angle of incidence.

11. The spectrometer of claim 1 wherein the filter matrix is composed of interference filters.

12. The spectrometer of claim 1 wherein the filters in the filter matrix are arranged in a specific order to minimize cross talk on the detector of light emerging from different filters.

13. The spectrometer of claim 1 further comprising an opaque absorbing aperture array between the filter matrix and the detector.

14. The spectrometer of claim 1 where spectra of each of a plurality of filters in the matrix overlaps another filter of the plurality of filters in the matrix.

15. The matrix of claim 14 wherein the overlap allows stitching of spectra generated by two different filters.

16. The spectrometer of claim 1 further comprising an illumination system.

17. The spectrometer of claim 16 wherein the illumination system comprises LEDs.

18. The spectrometer of claim 1 further comprising a thermal sensor capable of measuring a sampled material's temperature.

19. The spectrometer of claim 1 further comprising a reference element in front of the spectrometer.

20. The spectrometer of claim 1 wherein the detector comprises one or more of a 2D CMOS sensor or a 2D CCD sensor.

21. The spectrometer of claim 20 wherein the multiple sensors comprise pixels on the one or more of the 2D CMOS sensor or the 2D CCD sensor.

* * * * *